(12) United States Patent
Sofranko et al.

(10) Patent No.: US 10,968,149 B2
(45) Date of Patent: Apr. 6, 2021

(54) ENHANCED OXYGEN TRANSFER AGENT SYSTEMS FOR OXIDATIVE DEHYDROGENATION OF HYDROCARBONS

(71) Applicant: EcoCatalytic Inc., Monmouth Junction, NJ (US)

(72) Inventors: John A. Sofranko, Weston, MA (US); Royce Macwan, Edison, NJ (US); Elena Y. Chung, Somerville, MA (US); C. Andrew Jones, Newtown Square, PA (US)

(73) Assignee: EcoCatalytic Inc., Woburn, MA (US)

( * ) Notice: Subject to any disclaimer, the term of this patent is extended or adjusted under 35 U.S.C. 154(b) by 0 days.

(21) Appl. No.: 16/307,270

(22) PCT Filed: Jun. 27, 2017

(86) PCT No.: PCT/US2017/039448
§ 371 (c)(1),
(2) Date: Dec. 5, 2018

(87) PCT Pub. No.: WO2018/005456
PCT Pub. Date: Jan. 4, 2018

(65) Prior Publication Data
US 2020/0062677 A1 Feb. 27, 2020

Related U.S. Application Data
(60) Provisional application No. 62/355,740, filed on Jun. 28, 2016.

(51) Int. Cl.
*C07C 5/46* (2006.01)
*C07C 2/84* (2006.01)
(Continued)

(52) U.S. Cl.
CPC .............. *C07C 5/46* (2013.01); *B01J 27/055* (2013.01); *B01J 35/002* (2013.01); *C07C 2/84* (2013.01);
(Continued)

(58) Field of Classification Search
None
See application file for complete search history.

(56) References Cited

U.S. PATENT DOCUMENTS 4,544,785 A * 10/1985 Withers .................... C07C 2/84
585/415
4,670,619 A * 6/1987 Withers, Jr. .............. C07C 2/84
585/500

(Continued)

FOREIGN PATENT DOCUMENTS

| WO | 2015168601 A2 | 11/2015 |
| WO | 2016049144 A1 | 3/2016 |
| WO | 2016134305 A1 | 8/2016 |

OTHER PUBLICATIONS

Borry et al., "Non-Oxidative Conversion of Methane with Continuous Hydrogen Removal", Dec. 31, 1997, retrieved on Aug. 24, 2017, from https://www.osti.gov/scitech/biblio/620594—pp. 1-23.
(Continued)

*Primary Examiner* — Philip Y Louie
(74) *Attorney, Agent, or Firm* — RatnerPrestia

(57) ABSTRACT

Aspects of the invention relate to enhanced oxygen transfer agent systems and methods of use thereof. According to one aspect, a method for producing olefins from a hydrocarbon feed includes the step of contacting a hydrocarbon feed comprised of one or more alkanes with an oxygen transfer agent at a temperature of 350° C. to 1000° C. The oxygen transfer agent comprising an oxygen-donating chalcogen agent comprised of at least one of S, Se, or Te and a reducible metal oxide. The chalcogen having an oxidation
(Continued)

300

310 → Contact a hydrocarbon feed comprised of one or more alkanes and a gaseous oxygen-donating sulfur agent having an oxidation state greater than +2 with an oxygen transfer agent comprised of a reducible metal oxide at a temperature of 350°C to 1000°C 120 → Oxidize the reduced oxygen transfer agent to regenerate the oxygen transfer agent state greater than +2. According to another aspect, a method for producing one or more olefins by partial combustion of a hydrocarbon feed includes partially combusting a hydrocarbon feed comprised of one or more alkanes by contacting the hydrocarbon feed with an oxygen transfer agent comprising $CaSO_4$ at a temperature of 350° C. to 1000° C. to produce one or more olefins comprising ethylene and coproducing water.

23 Claims, 5 Drawing Sheets

(51) Int. Cl.
  *B01J 27/055* (2006.01)
  *B01J 35/00* (2006.01)
  *C07C 11/04* (2006.01)

(52) U.S. Cl.
  CPC .......... *C07C 11/04* (2013.01); *C07C 2521/10* (2013.01); *C07C 2523/04* (2013.01); *C07C 2523/34* (2013.01); *C07C 2527/053* (2013.01)

(56) References Cited

U.S. PATENT DOCUMENTS

| | | | |
|---|---|---|---|
| 4,777,313 A * | 10/1988 | Sofranko | B01J 23/08 585/500 |
| 4,879,427 A | 11/1989 | Sofranko | |
| 4,939,312 A * | 7/1990 | Baerns | C07C 2/84 585/500 |
| 8,835,346 B2 | 9/2014 | Gramiccioni et al. | |
| 2003/0181325 A1* | 9/2003 | Ou | B01J 23/002 502/302 |

OTHER PUBLICATIONS

International Preliminary Report on Patentability for International Application No. PCT/US2017/039448, dated Jan. 1, 2019—7 pages.
International Search Report and Written Opinion for International Application No. PCT/US2017/039448, dated Sep. 8, 2017—8 pages.
Zhu et al., "Sulfur as a Selective 'Soft' Oxidant for Catalytic Methane Conversion Probed by Experiment and Theory", Nature Chemistry, Feb. 2013, vol. 5, pp. 104-109.
Ding et al., "Effect of Hematite Addition to $CaSO_4$ Oxygen Carrier in Chemical Looping Combustion of Coal Char", Royal Society of Chemistry, 2015, vol. 5, pp. 56362-56376.
Levasseur et al., "Alstom's [GE] Chemical Looping Combustion Technology wtih $Co_2$ Capture for New and Existing Coal-Fired Power Plants", 2016 NETL $Co_2$ Capture Technology Meeting, Aug. 8-12, 2016, 18 pages.

\* cited by examiner

ENHANCED OXYGEN TRANSFER AGENT SYSTEMS FOR OXIDATIVE DEHYDROGENATION OF HYDROCARBONS

CROSS REFERENCE TO RELATED APPLICATIONS

This application is a U.S. National Phase Application of PCT International Application PCT/US2017/039448, filed on Jun. 27, 2017, which claims priority to and benefit of U.S. Provisional Patent Application No. 62/355,740, filed Jun. 28, 2016, the disclosures of which are incorporated herein by reference in their entireties for all purposes.

STATEMENT REGARDING FEDERALLY SPONSORED RESEARCH

This invention was made with government support under grant number DE-AR0000327 awarded by the Department of Energy. The government has certain rights in the invention.

FIELD OF THE INVENTION

The present invention relates to enhanced oxygen transfer agent systems, and particularly, enhanced sulfur oxygen transfer agent systems and methods for using such systems for the oxidative dehydrogenation of hydrocarbons.

BACKGROUND OF THE INVENTION

Ethylene and propylene are important building blocks for the petrochemical industry. These olefins are used in the manufacturing of polymers such as polyethylene, polypropylene, polystyrene and many more chemicals of commercial interest. Over 90% of global olefin production may come from the high temperature steam cracking of naphtha or ethane and propane. The steam cracking process, which utilizes furnaces, is highly energy intensive, and 1.5 to 2 tons of carbon dioxide is produced for every ton of olefin product.

Natural gas production from shale deposits has dramatically increased supply in recent years. As a result of the continued global demand for olefins and the potential for a new growing supply of ethane and propane available in natural gas liquids from shale deposits, a significant amount of interest and investment is currently centered around expanding the capacity of ethylene and propylene derived from these new sources. However, there are many environmental and cost challenges associated with processes for deriving ethylene and propylene from natural gas liquids.

Olefin production is the largest emitter of $CO_2$ and $NO_x$ in the organic chemical industry. With worldwide ethylene production at ~150 MT/yr, the industry emits 150-300 MT/yr of $CO_2$ and roughly 1.4 MT/yr of $NO_x$. Projects located in severe EPA non-attainment zones are challenged by the increased cost of $NO_x$ control. The total greenhouse gas (GHG) emission profile, reported in $CO_2$ equivalents, is another critical part of the permitting for all production expansions.

It is well understood that olefin production from natural gas liquids using oxidative transformation processes is limited by several over-oxidation pathways. Specifically, the desired olefin products may be far more reactive with the oxygen molecules than the methane and/or hydrocarbon feed, which results in rapid conversion of the desired olefin products to more thermodynamically stable undesired byproducts, such as $CO_2$. Additionally, traditional oxidative transformation processes using oxygen molecules typically increase local temperatures within the reactions by 150-300° C., thereby presenting significant heat management and reactor design issues.

Accordingly, in recent years, processes for producing olefins have relied upon the weaker C—S and H—S bonds as well as lower bond enthalpies resulting from use of $S_2$ as an oxidant. Specifically, it is conventional wisdom that the bonds between H—S provides benefits over processes where oxygen is reacted with hydrocarbons.

There is a long standing need for improved systems and methods for efficiently producing olefins from hydrocarbon feeds.

SUMMARY OF THE INVENTION

Aspects of the invention relate to enhanced oxygen transfer agent systems and methods of use thereof.

In accordance with one aspect of the invention, a method for producing one or more olefins from a hydrocarbon feed comprised of one or more alkanes includes the step of contacting a hydrocarbon feed comprised of one or more alkanes with an oxygen transfer agent at a temperature of 350° C. to 1000° C. The oxygen transfer agent comprises an oxygen-donating chalcogen agent comprised of at least one of S, Se, or Te and a reducible metal oxide. The chalcogen has an oxidation state greater than +2.

According to another aspect of the invention, a method for producing one or more olefins by partial combustion of a hydrocarbon feed comprised of one or more alkanes includes partially combusting a hydrocarbon feed comprised of one or more alkanes by contacting the hydrocarbon feed with an oxygen transfer agent at a temperature of 350° C. to 1000° C. to produce one or more olefins comprising ethylene and coproducing water. The oxygen transfer agent comprises $CaSO_4$.

In accordance with a further aspect of the invention, a method for producing one or more olefins from a hydrocarbon feed comprised of one or more alkanes includes a step of contacting a hydrocarbon feed comprised of one or more alkanes and a gaseous oxygen-donating sulfur agent with an oxygen transfer agent comprised of a reducible metal oxide at a temperature of 350° C. to 1000° C. The gaseous oxygen-donating sulfur agent has an oxidation state greater than +2.

BRIEF DESCRIPTION OF THE FIGURES

The invention is best understood from the following detailed description when read in connection with the accompanying drawings, with like elements having the same reference numerals. Included in the drawings are the following figures.

DETAILED DESCRIPTION OF THE INVENTION

The inventors have discovered that employing particular compositions for oxygen transfer agents enables methods for producing olefins by oxidative dehydrogenation of hydrocarbons (hereafter "ODH") that have highly advantageous yields and improved selectivity of desired products. These ODH processes produce olefins from hydrocarbon feeds, e.g., methane, ethane, propane, etc., while producing significantly less $CO_2$ emissions and virtually no $NO_x$ emissions as compared to conventional processes, such as hydrocarbon cracking. Advantageously, methods in accordance with the invention may be modified to improve the selectivity for specific products, such as ethane, ethylene, $C_3^+$ hydrocarbons, and/or water.

One of the main reaction mechanisms of ODH processes is shown below (reaction 1).

$$CH_3CH_3 + \tfrac{1}{2}O_2 \rightarrow CH_2CH_2 + H_2O \ \Delta H_o = -105 \text{ kJ/mol} \quad (1)$$

The per pass yield of the ODH reaction is not limited by thermodynamic equilibrium, as it is in pyrolysis, (reaction 2).

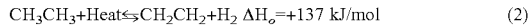

$$CH_3CH_3 + \text{Heat} \leftrightarrows CH_2CH_2 + H_2 \ \Delta H_o = +137 \text{ kJ/mol} \quad (2)$$

The inventors have now recognized that employing specific oxygen transfer agents under particular method conditions results in high selectivity to desired olefins. Accordingly, aspects of the present invention include oxygen transfer agents and methods employing such oxygen transfer agents.

In one aspect of the invention, a method is provided for producing olefins from a hydrocarbon feed by ODH using a sulfur enhanced oxygen transfer agent. Contrary to conventional wisdom regarding sulfur oxidants used for ODH processes, the inventors have surprisingly discovered that oxygen transfer agents containing the sulfur compounds disclosed herein donate oxygen during ODH processes, which improves the selectivity and yield of desired olefin production. Moreover, the oxygen transfer agents disclosed herein have a significantly lower selectivity for reaction pathways resulting in over-oxidation of the hydrocarbon feed, which is common with ODH processes using oxygen as the oxidative. It is commonly believed that the high oxygen transfer capacity of oxidizing agents comprising oxygen is a non-selective process application that results in the total combustion of hydrocarbons to carbon dioxide and water. These oxidizing agents comprising oxygen are conventionally used at temperature >1,000° C.

In another aspect of the invention, provided is a method for producing olefins from a hydrocarbon feed by ODH using an oxygen transfer agent comprising an oxygen-donating chalcogen agent and a reducible metal oxide. Employing an oxygen transfer agent comprising an oxygen-donating chalcogen agent and a reducible metal oxide provided highly advantageous results that surprised the inventors.

Figure 1:
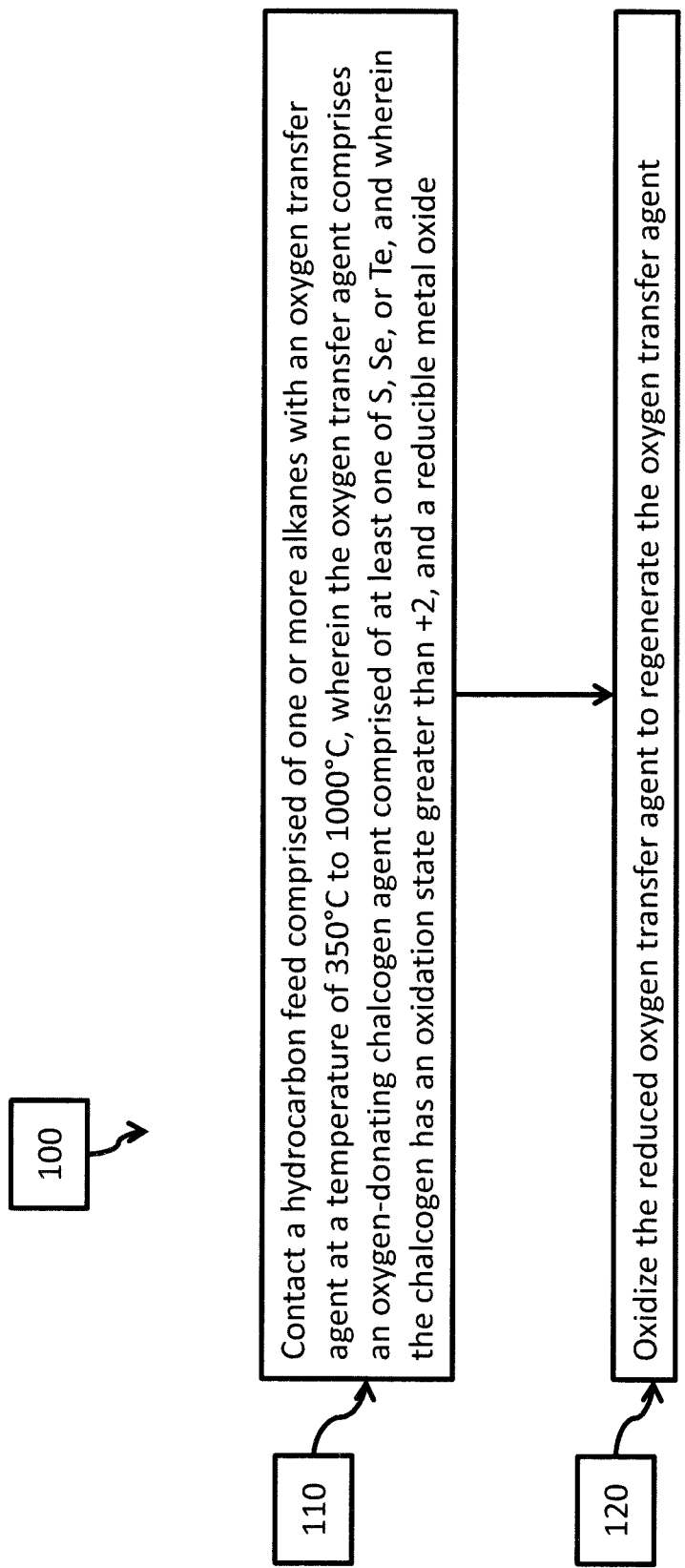
FIG. 1 illustrates a method for producing one or more olefins from a hydrocarbon feed comprised of one or more alkanes in accordance with aspects of the invention.

FIG. 1 illustrates a method 100 for producing one or more olefins from a hydrocarbon feed comprised of one or more alkanes according to an embodiment of the invention. In step 110 a hydrocarbon feed comprised of one or more alkanes is contacted with an oxygen transfer agent at a temperature of 350° C. to 1000° C. The oxygen transfer agent comprises an oxygen-donating chalcogen agent comprised of at least one of S, Se, or Te, wherein the chalcogen has an oxidation state greater than +2, and a reducible metal oxide.

The hydrocarbon feed may, for example, include one or more saturated aliphatic hydrocarbons (alkanes) such as at least one of methane or ethane. Substances other than alkanes may also be present in the hydrocarbon feed. For example, the hydrocarbon feed may be natural gas obtained from unconventional well drilling techniques. In one embodiment, the hydrocarbon feed is natural gas having, e.g., at least 70% methane by volume, at least 80% methane by volume, or at least 90% methane by volume. Under at least certain reaction conditions, methane may undergo oxidative coupling and possibly dehydrogenation to form higher hydrocarbons such as ethane and/or ethylene. In another embodiment, the hydrocarbon feed includes at least 30% ethane, preferably at least 40% ethane, preferably at least 50% ethane, preferably at least 60% ethane, preferably at least 70% ethane, preferably at least 80% ethane, or preferably at least 90% ethane.

Method 100 may be employed to produces one or more olefins, e.g., ethylene, and coproduce water. For example, method 100 may produce ethylene in a selectivity of 60% or more. In one embodiment, method 100 has a selectivity to ethylene of 65% or more, 67% or more, 70% or more, 80% or more, 85% or more, or 90% or more.

The coproduction of water indicates a desirable selectivity of the oxygen transfer agent, favoring reaction mechanisms that produce water instead of hydrogen gas. For example, large amounts of water coproduction may indicate that the oxygen transfer agent has a high selectivity for donating an oxygen atom to the hydrocarbon feed molecules, which facilitates removal of hydrogen atoms from the hydrocarbon feed molecule and, thereby, supports ODH. Thus, the co-product water is preferably formed from oxygen donated by the oxygen transfer agent. For example, in one embodiment, at least 49% by mole of the hydrocarbon feed is converted to oxides of carbon, whereby water is produced as a co-product. In another embodiment, at least 49% by mole of the hydrocarbon feed is converted to olefins, whereby water is produced as a co-product. Preferably, method 100 produces more water than hydrogen on a molar basis. For example, the molar ratio of water to hydrogen may be at least 1:1, preferably at least 2:1, preferably at least 3:1, preferably at least 4:1, preferably at least 5:1, preferably at least 6:1, preferably at least 7:1, preferably at least 8:1, preferably at least 9:1, preferably at least 10:1, preferably at least 11:1, preferably at least 12:1, or preferably at least 13:1.

The oxygen transfer agent may include at least one oxygen-donating chalcogen agent and at least one reducible metal oxide. The oxygen-donating chalcogen agent(s) and reducible metal oxide(s) may be integrally dispersed (e.g., uniformly dispersed) within the oxygen transfer agent. In one embodiment, the oxygen-donating chalcogen agent(s) and the reducible metal oxide(s) may form the active compounds of the oxygen transfer agent, e.g., such that the oxygen-donating chalcogen agent(s) and the reducible metal oxide(s) are the only compounds actively transferring oxygen to the hydrocarbon feed. The oxygen transfer agent may consist of the at least one oxygen-donating chalcogen agent and at least one reducible metal oxide, optionally together with at least one inert binder or support. One or more of the oxygen-donating chalcogen agent(s) and the reducible metal oxide(s) may be in solid form. In one embodiment, the oxygen-donating chalcogen agent(s) and the reducible metal oxide(s) are integrally part of a solid substance, e.g., a solid substance forming a crystalline lattice structure, or amorphous, or partially crystalline structure containing both the oxygen-donating chalcogen agent and the metal oxide. The oxygen transfer agent may also include boron or at least one compound thereof. In one embodiment, the oxygen transfer agent additionally includes $Mg_6MnO_8$ and/or at least one promoter selected from the group consisting of Sm, Ga, Ti, W, Mo, V, Nb, Cr, K, Cs, Rb, P, Cu, Pb, Ni, and As.

The oxygen-donating chalcogen agent is preferably comprised of sulfur, although tellurium and/or selenium may alternatively or additionally be present. For example, the oxygen-donating chalcogen agent may include at least one of a sulfate salt of an alkaline earth metal or a sulfate salt of an alkali metal. For example, the sulfate anion may be balanced with a cation, such as sodium, lithium, etc. In one embodiment, the oxygen-donating chalcogen agent may include a sulfate salt of manganese. In another embodiment, the oxygen-donating chalcogen agent includes calcium sulfate. The oxygen donating chalogen may be a sulfate salt including Sn, Ga, Tl, W, Mo, V, Nb, Cr, K, Cs, Rb, P, Cu, Pb, Ni, and/or As. The chalcogen of the oxygen-donating chalcogen agent has an oxidation state of +3 to +6. Alternatively, the chalcogen of the oxygen-donating chalcogen agent has an oxidation state greater than +3 and less than +6. In one embodiment, however, the chalcogen of the oxygen-donating chalcogen agent has an oxidation state of +4. In another embodiment, the oxygen transfer agent comprises, consists essentially of, or consists of $CaSO_4$ (calcium sulfate).

The oxygen transfer agent may comprise at least one alkali metal, alkali earth metal, or a compound thereof. For example, the oxygen transfer agent may include at least one of an alkali metal oxide or an alkaline earth metal oxide. For example, the oxygen transfer agent may include a metal oxide comprised of titanium, lanthanum, cerium, zinc, copper, vanadium, manganese, and/or any compound thereof. Preferably, the reducible metal oxide comprises a manganese oxide having a valence state of 4+, 3+, 8/3+, or 2+. For example, the reducible metal oxide may comprise a) at least one compound selected from the group consisting of $NaB_2Mg_4Mn_2O_4$, $NaB_2Mn_2Mg_4O_{11.5}$, $NaMn_2O_4$, $LiMn_2O_4$, $Mg_3Mn_3B_2O_{10}$, $Mg_3(BO_3)_2$, and b) a non-crystalline compound comprising oxygen and at least one of sodium, boron, magnesium, manganese, or lithium. In addition to being reducible, the metal oxide may be ionically and electronically conductive.

The inventors were surprised by the advantageous selectivity and yields achieved by method 100 with an oxygen transfer agent comprising a sulfate and a manganese metal oxide. The inventors have discovered that by employing the oxygen transfer agents comprising a sulfur oxide compound and a manganese metal oxide with certain processing conditions, such as reaction temperatures, improved olefin selectivity and yields may be obtained while advantageously reducing the reducing the amount of carbon dioxide produced. In one embodiment, the sulfur oxide compound and the metal oxide are integrally dispersed in the oxygen transfer agent. The sulfur oxide compound may be bonded to the metal oxide (e.g., the sulfur compound may be dressed to the oxide or the oxide may be dressed to the sulfur compound) and/or the sulfur oxide may be in intimate proximity to the metal oxide to form an intimate mixture.

The contacting step of 110 may occur in an atmosphere that is substantially free of molecular oxygen. For example, the hydrocarbon feed may contact the oxygen transfer agent in an atmosphere having less than 5% molecular oxygen by volume, e.g., less than 2% molecular oxygen, less than 1% molecular oxygen, or less than 0.5% molecular oxygen by volume. Method 100 may be adapted to provide improved yields of desirable olefins when the hydrocarbon feed is contacted with oxygen transfer agent in an atmosphere substantially free of molecular oxygen. As used herein, an atmosphere substantially free of molecular oxygen means an atmosphere having less than 3% molecular oxygen by volume. Method 100, however, may also be adapted so that the hydrocarbon feed contacts the oxygen transfer agent in in the presence of molecular oxygen.

The contacting step of 110 occurs at a temperature of 350° C. to 1000° C. For example, the hydrocarbon feed may contact the oxygen transfer agent at a temperature of 400° C. to 975° C., 500° C. to 950° C., or 650° C. to 900° C. The temperature may be held constant or varied within the desired temperature range.

Method 100 may also include step 120 for oxidizing the reduced oxygen transfer agent to regenerate the oxygen transfer agent. In an embodiment of the invention, the oxygen transfer agent is converted to a reduced oxygen transfer agent during contacting step 110. The oxygen transfer agent may be oxidized and/or regenerated using, e.g., an oxygen-containing gas stream, such as air, super-heated steam, substantially pure molecular oxygen, etc. Additionally and/or alternatively, method 100 may include a feed comprising a gaseous compound of sulfur, the gaseous compound of sulfur having an oxidation state of 0 to −2, which acts to stabilize the oxygen donating agent. Exemplary gaseous compounds of sulfur suitable for use in the present invention include hydrogen sulfide.

Method 100 may also include a step for regenerating an oxygen transfer agent containing sulfur by contacting the oxygen transfer agent with a feed of sulfur compounds, e.g., a gaseous stream of sulfur compound. In one embodiment, the feed of sulfur compound is continuously introduced into the reactor, such that the oxygen transfer agent may continually be in contact with the stream of sulfur compounds. For example, in order to maintain a suitable sulfur level in the oxygen transfer agent comprising sulfur under the conditions of certain embodiments of this invention, it may be beneficial to replenish the sulfur oxygen transfer agent by feeding a gaseous stream of a sulfur comprising gas. The gaseous sulfur compounds may include $H_2S$, $SO_2$, $SO_3$, $S_8$, or any sulfur containing gas that acts to replenish and stabilize an oxygen transfer agent comprising sulfur.

Figure 2:
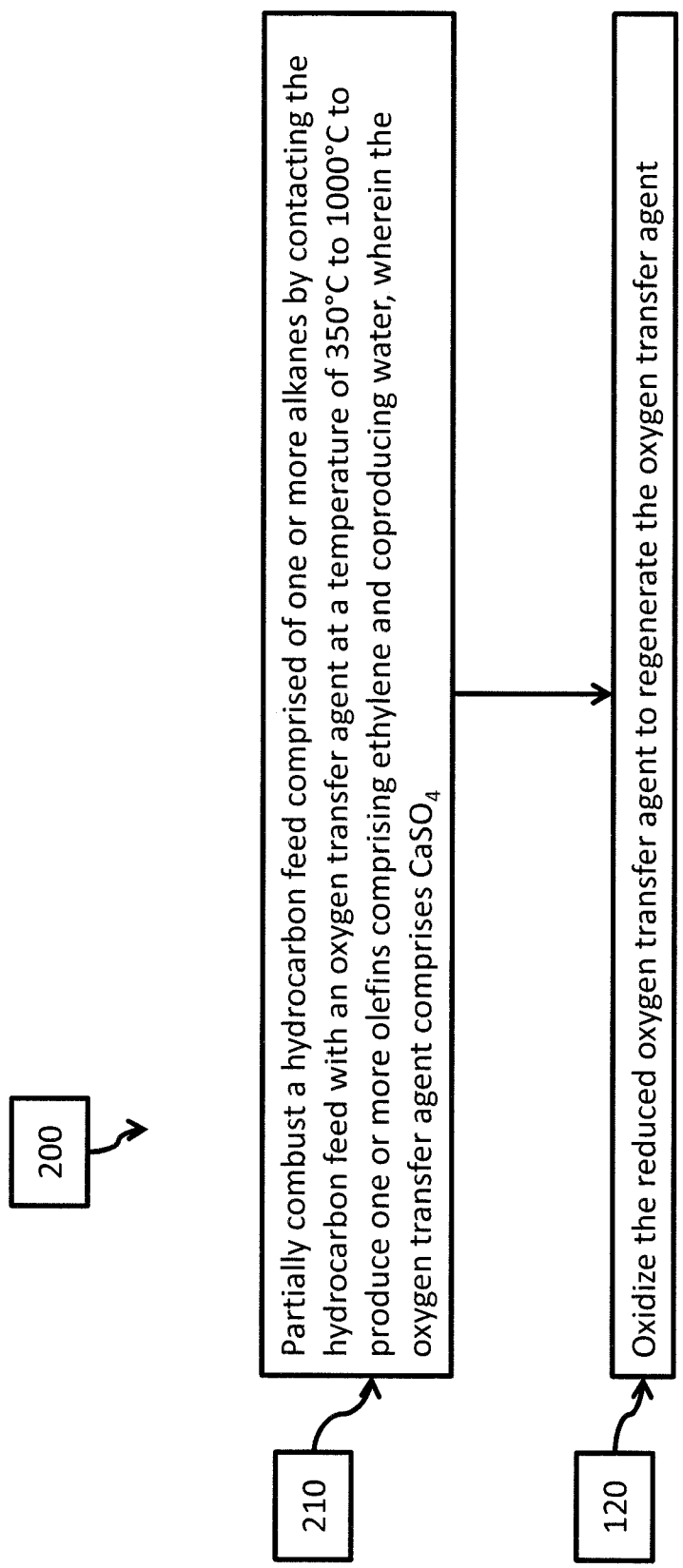
FIG. 2 illustrates a method for producing one or more olefins by partial combustion of a hydrocarbon feed comprised of one or more alkanes according to an aspect of the invention.
Figure 3:
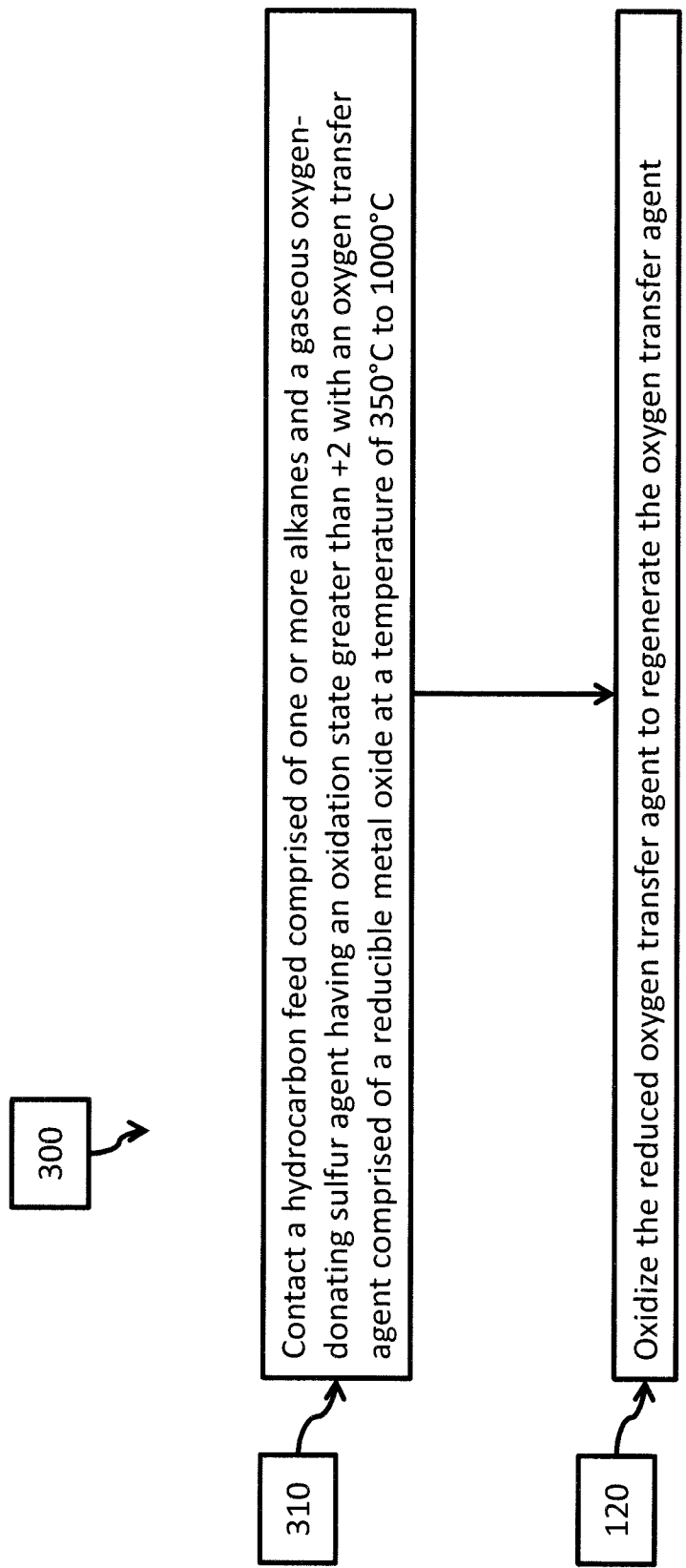
FIG. 3 illustrates a method for producing one or more olefins from a hydrocarbon feed comprised of one or more alkanes in accordance with an aspect of the invention.

FIGS. 2 and 3 illustrate two non-limiting methods according to aspects of the invention. Although methods 200 and 300 have similarities to method 100, methods 200 and 300 include the differences disclosed herein. Accordingly, various specifics of methods 200 and 300 may be omitted if similar to method 100.

FIG. 2 illustrates a method 200 for producing one or more olefins by partial combustion of a hydrocarbon feed comprised of one or more alkanes according to an aspect of the invention. In step 210, a hydrocarbon feed comprised of one or more alkanes is partially combusted with an oxygen transfer agent at a temperature of 350° C. to 1000° C. to produce one or more olefins comprising ethylene and coproducing water. In one embodiment, the oxygen transfer agent comprises, consists essentially of, or consists of $CaSO_4$. In one aspect of the invention, the oxygen transfer does not contain any reducible metal oxide.

FIG. 3 illustrates a method 300 for producing one or more olefins from a hydrocarbon feed comprised of one or more alkanes in accordance with an aspect of the invention. In step 310, a hydrocarbon feed comprised of one or more alkanes is contacted with a gaseous oxygen-donating sulfur agent having an oxidation state greater than +2 with an oxygen transfer agent comprised of a reducible metal oxide at a temperature of 350° C. to 1000° C. The oxygen-donating sulfur agent may be an oxide of sulfur, such as $SO_2$, $SO_3$, or the like.

The oxygen transfer agents disclosed herein may be prepared by any methods known by those skilled in the art, including, but not limited to, precipitation, co-precipitation, impregnation, granulation, spray drying, dry mixing, etc. Precursors may be transformed into active agents by calcination at temperatures suitable for the formation of the active components, e.g., in the range of 4000 to 1,100° C. The calcination may be performed under any atmosphere, such as air, inert gases, hydrogen, carbon monoxide, and hydrocarbon gases, so as to form the active oxygen transfer agents of the present invention. The oxygen transfer agent may be admixed or otherwise formulated with binders, supports, carriers and the like using any conventional procedures known in the art and may be utilized in any suitable shape or physical form such as powder, granules, pellets, beads, rings, monoliths, extrudates and the like.

Aspects of the present invention include systems employing the methods disclosed herein. The systems may include a reactor containing an oxygen transfer agent useful for the methods described herein. The system may include any reactor type known to be useful for the selective oxidation or dehydrogenation of hydrocarbons. For example, the oxygen transfer agent may be employed in a bed in a reactor with the gas hourly space velocity of the hydrocarbon feed to the bed being at least 600 $hr^{-1}$ (or per hour). In one embodiment, the gas hourly space velocity of the hydrocarbon feed to the bed is at least 800 hr, at least 1,400 $hr^{-1}$, at least 1,600 $hr^{-1}$, at least 1,800 $hr^{-1}$, at least 2,000 $hr^{-1}$, at least 2,200 $hr^{-1}$, at least 2,400 $hr^{-1}$, at least 2,600 $hr^{-1}$. In another embodiment, the gas hourly space velocity of the hydrocarbon feed to the bed is 5,800 $hr^{-1}$ or less, 5,600 $hr^{-1}$ or less, 5,400 $hr^{-1}$ or less, 5,200 $hr^{-1}$ or less, 5,000 $hr^{-1}$ or less, or 4,800 $h^{-1}$ or less.

The oxygen transfer agents according to various embodiments of the present invention may be used in a chemical looping system to promote an ODH reaction via a Mars-van Krevelen-like mechanism. The effective utilization of the chemical looping mode of this invention may be performed, for example, in either fixed or circulating bed reactors. In the case of fixed bed reactors, multiple reactors may be used such that hydrocarbon oxidation and the re-oxidation of the oxygen transfer agent are occurring continuously as feed and air is alternately cycled to multiple reactors. In the instance where the conversions of Equation 1 are run in a co-feed mode with a mixture of hydrocarbon and oxidant, it will be useful to use reactors that can effectively remove the heat of reaction, such as shell and tube reactors.

EXAMPLES

The following examples are non-limiting embodiments of the present invention, included herein to demonstrate the advantageous utility obtained from aspects of the present invention.

Example 1

An oxygen transfer agent was prepared by mixing (in a ball mill) manganese oxide (32.2 g), boric acid (11.5 g), magnesium oxide (41.8 g) and lithium hydroxide (4.5 g) with sufficient water to make a paste. The paste was dried for 4 hours at 110° C. and then calcined in air at 950° C. for 8 hours. The oxygen transfer agent preparation was sized to 14-30 mesh and 5 ml charged to 0.75 inch OD alpha alumina reactors. The results of the olefin productions from a hydrocarbon feed are shown below in Table 1.

The results of Table 1 include conversions, selectivities, and yields. These are calculated on a carbon mole basis. Space velocities are reported as gas hourly space velocities ($hr^{-1}$) calculated at standard conditions and shown as GHSV. For these examples, hydrocarbon feeds were pulsed for 15 seconds and the total product gas collected in a gas bag for GC analysis. After hydrocarbon pulses, the reactors were purged for 5 minutes with nitrogen and exposed to a flow of air for 10 minutes. Both the nitrogen and air flows were matched to the run GHSV. This cycle was repeated up to 150 cycles.

TABLE 1

| TABLE I | | | | | |
|---|---|---|---|---|---|
| | Temp., ° C. | 825 | 825 | 840 | 840 |
| | GHSV, $hr^{-1}$ | 2,400 | 4,800 | 2,400 | 4,800 |
| % Selectivity | Methane | 6.25% | 4.78% | 7.42% | 5.51% |
| | Ethylene | 48.86% | 67.97% | 47.92% | 66.41% |
| | Acetylene | 1.75% | 1.31% | 2.29% | 1.60% |
| | Propylene | 1.68% | 1.97% | 1.59% | 1.83% |
| | Propadiene | 0.03% | 0.02% | 0.03% | 0.03% |
| | Propane | 0.34% | 0.47% | 0.24% | 0.34% |
| | Methyl Acetylene | 0.30% | 0.22% | 0.37% | 0.28% |
| | C4's | 4.22% | 4.83% | 4.03% | 4.69% |
| | C5's | 0.14% | 0.21% | 0.10% | 0.17% |
| | $C6^+$'s | 11.59% | 7.53% | 9.76% | 8.53% |
| | Coke | ND | ND | ND | ND |
| % Conversion | Ethane | 92.48% | 76.97% | 94.11% | 79.98% |
| % Selectivity | $C_2^+$ | 68.91% | 84.53% | 66.33% | 83.87% |
| % Yield | $C_2^+$ | 63.73% | 65.07% | 62.42% | 67.08% |
| % Selectivity | Carbon Dioxide | 21.20% | 8.69% | 22.11% | 8.67% |
| | Carbon Monoxide | 3.65% | 1.99% | 4.14% | 1.95% |
| % Yield | Carbon Dioxide | 19.61% | 6.69% | 20.81% | 6.93% |
| | Carbon Monoxide | 3.37% | 1.53% | 3.90% | 1.56% |
| % Selectivity | % $H_2$ Selectivity | 4.03% | 12.57% | 4.30% | 12.33% |
| | % $H_2O$ Selectivity | 95.97% | 87.43% | 95.70% | 87.67% |

After each run, during the air regeneration, a sample of the reactor off gas was analyzed for carbon dioxide and carbon monoxide to indicate possible coke formation during the cycle. In all experiments coke was not detected. In the absence of the oxygen transfer agent, the $H_2$ selectivity equaled 100%. This example shows some of the benefits of using an oxygen transfer agent employed in a method in accordance with aspects of the invention for the production of olefins by way of ODH.

Example 2

An oxygen transfer agent was prepared according to the processing steps for preparing the oxygen transfer agent of Example 1, but included the addition of $CaSO_4$ (31.9 g). All other ox preparation and run procedures were identical to Example 1. The results of the olefin productions from a hydrocarbon feed, including the conversion of ethane, are shown in Table 2.

ethane produces water as a coproduct. However, a mixture of $CaSO_4$ and a manganese oxide material, as in Example 2, is more active, giving higher olefin yields and higher hydrogen conversion to water at comparable conditions. Surprisingly, while methods in accordance with embodiments using solely $CaSO_4$ or a manganese oxide material provided an olefin yield of 62.1% and 63.73%, the method in accordance with an embodiment using an oxygen transfer agent having $CaSO_4$ and a manganese oxide material provided an olefin yield of 75.65%, which represents an improvement of the yield of at least 18.7%.

TABLE 2

| TABLE II | | | | | |
|---|---|---|---|---|---|
| | Temp. (° C.) | 825 | 825 | 840 | 840 |
| | GHSV, (hr$^{-1}$) | 2,400 | 4,800 | 2,400 | 4,800 |
| Selectivity (%) | Methane | 9.69% | 5.88% | 11.92% | 7.24% |
| | Ethylene | 64.95% | 76.98% | 58.35% | 73.28% |
| | Acetylene | 0.83% | 0.45% | 1.21% | 0.70% |
| | Propylene | 3.07% | 2.87% | 2.65% | 2.74% |
| | Propadiene | 0.06% | 0.04% | 0.07% | 0.05% |
| | Propane | 0.74% | 0.72% | 0.56% | 0.61% |
| | Methyl Acetylene | 0.27% | 0.17% | 0.33% | 0.23% |
| | C4's | 7.08% | 6.75% | 6.66% | 6.99% |
| | C5's | 2.48% | 2.02% | 2.32% | 2.26% |
| | C6$^+$'s | 7.17% | 2.80% | 10.03% | 4.19% |
| | Coke | ND | ND | ND | ND |
| Conversion (%) | Ethane | 87.31% | 71.62% | 92.48% | 79.63% |
| Selectivity (%) | C$_2^+$ | 86.64% | 92.81% | 82.16% | 91.06% |
| Improved selectivity as compared to Table 1 (%) | C$_2$+ | 25.7% | 9.8% | 23.9% | 8.6% |
| Yield (%) | C$_2$+ | 75.65% | 66.48% | 75.98% | 72.51% |
| Improved yield as compared to Table 1 (%) | C$_2^+$ | 18.7% | 2.2% | 21.7% | 8.1% |
| Selectivity (%) | Carbon Dioxide | 2.14% | 0.76% | 3.57% | 1.02% |
| | Carbon Monoxide | 1.53% | 0.55% | 2.34% | 0.69% |
| Yield (%) | Carbon Dioxide | 1.87% | 0.54% | 3.31% | 0.81% |
| | Carbon Monoxide | 1.34% | 0.39% | 2.17% | 0.55% |
| Reduction as compared to Table 1 (%) | Carbon Dioxide | 90.5 | 91.9 | 84.1 | 88.3 |
| | Carbon Monoxide | 60.2 | 74.5 | 44.4 | 64.7 |
| Selectivity (%) | H$_2$ Selectivity (%) | 26.07% | 41.04% | 19.94% | 37.74% |
| | H$_2$O Selectivity (%) | 73.93% | 58.96% | 80.06% | 62.26% |

Figure 4:
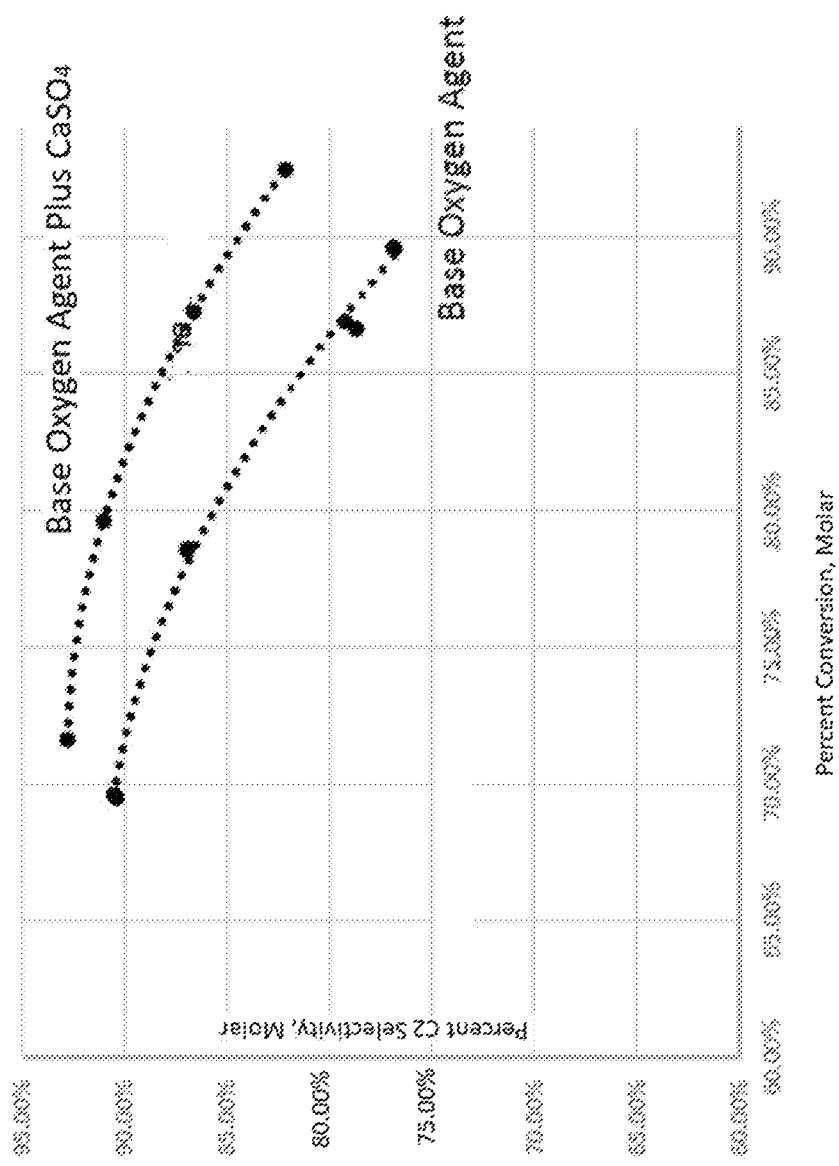
FIG. 4 is a graph illustrating the relationship between the conversion of ethane and the selectivity to the desired olefin products according to an aspect of the invention.

The yield to desired ethylene, and higher molecular weight unsaturated products in Example 2 is higher under each of the conditions as compared to Example 1. These higher yields demonstrate some of the beneficial effects of preparing an oxygen transfer agent having $CaSO_4$ in accordance with aspects of the invention. The relationship between the conversion of ethane and the selectivity to the desired products is shown in FIG. 4.

Figure 5:
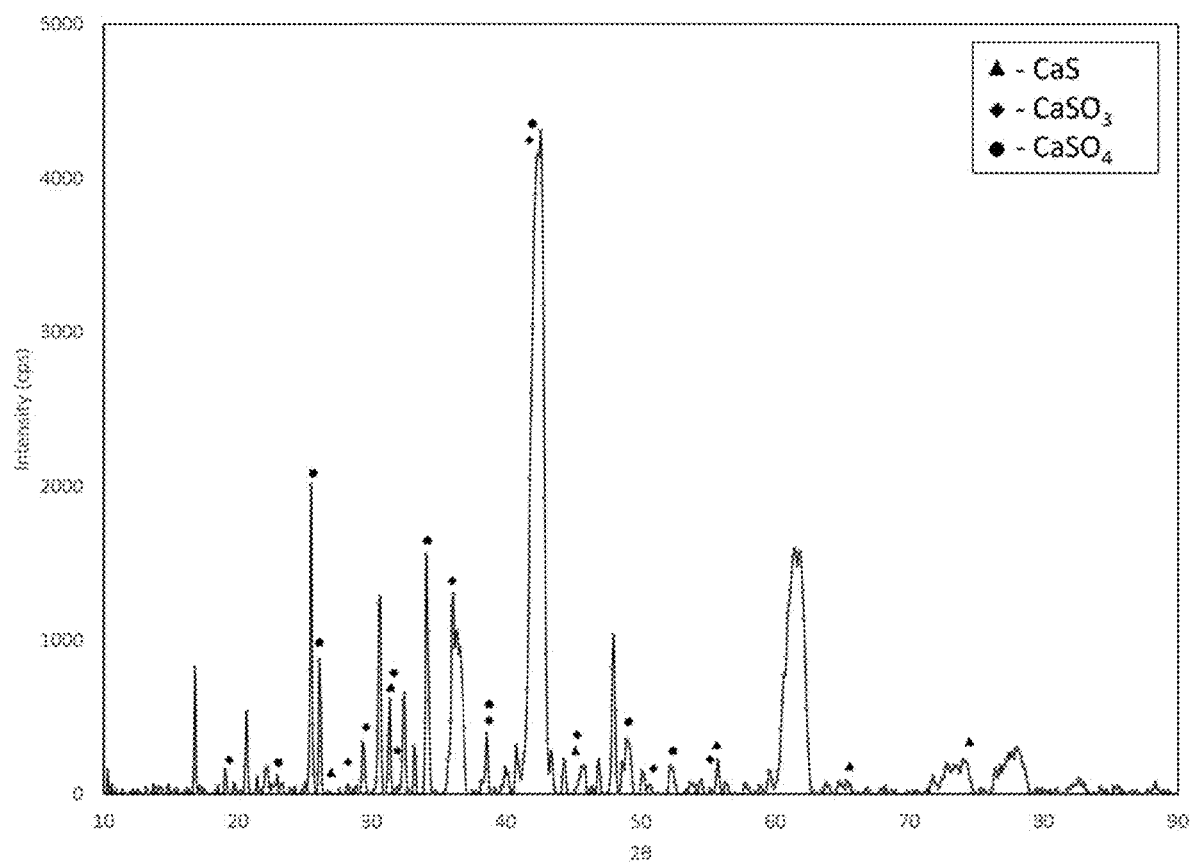
FIG. 5 is an x-ray diffraction graph of the used oxygen transfer agent of Example 2, which indicates the presence of reduced species of calcium sulfate, in accordance with an embodiment of the invention.

After the last ethane run of Example 2, the reactor was purged with nitrogen and returned to room temperature before the oxygen transfer agent was exposed to air. The used/spent oxygen transfer agent was characterized by x-ray diffraction ("XRD"), see FIG. 5. The XRD exhibits peaks indicating reducible forms of $CaSO_4$, which demonstrates the oxygen-donation of the sulfate amongst the reducible metal oxide by the reactions occurring in Example 2.

Example 3

Example 3 demonstrates that employing $CaSO_4$ as an oxygen transfer agent in a method in accordance with aspects of the invention for the oxidative dehydration of

TABLE 3

| TABLE III | OTA | From Example 2 | From Example 1 | CaSO$_4$ |
|---|---|---|---|---|
| | Temp., ° C. | 825 | 825 | 825 |
| | GHSV, hr$^{-1}$ | 2,400 | 2,400 | 2,400 |
| Selectivity (%) | Methane | 9.69% | 6.25% | 6.96% |
| | Ethylene | 64.95% | 48.86% | 79.82% |
| | Acetylene | 0.83% | 1.75% | 0.00% |
| | Propylene | 3.07% | 1.68% | 2.23% |
| | Propadiene | 0.06% | 0.03% | 0.38% |
| | Propane | 0.74% | 0.34% | 0.03% |
| | Methyl Acetylene | 0.27% | 0.30% | 0.17% |
| | C4's | 7.08% | 4.22% | 4.38% |
| | C5's | 2.48% | 0.14% | 0.60% |
| | C6$^+$'s | 7.17% | 11.59% | 4.60% |
| | Coke | ND | ND | ND |
| Conversion (%) | Ethane | 87.31% | 92.48% | 67.33% |
| Selectivity (%) | C$_2^+$ | 86.64% | 68.91% | 92.23% |
| Yield (%) | C$_2$+ | 75.65% | 63.73% | 62.10% |
| Selectivity (%) | Carbon Dioxide | 2.14% | 21.20% | 0.44% |
| | Carbon Monoxide | 1.53% | 3.65% | 0.37% |
| Yield (%) | Carbon Dioxide | 1.87% | 19.61% | 0.29% |
| | Carbon Monoxide | 1.34% | 3.37% | 0.25% |
| Selectivity (%) | H$_2$ Selectivity (%) | 26.07% | 4.03% | 80.64% |
| | H$_2$O Selectivity (%) | 73.93% | 95.97% | 19.36% |

Example 4

In this Example, the oxygen transfer agent from Example 1 was used for the conversion of methane to ethylene and higher olefins. The observed results, including the yield of $C2^+$ product, is shown below. This example shows some of the benefits of using an oxygen transfer agent in accordance with aspects of the invention. Comparing the results of Example 4 to Example 1 illustrates the improved selectivity and yield of olefins for methods using a feed of primarily ethane instead of a feed of primarily methane.

TABLE 4

| TABLE IV | Temp., (° C.) | 825 | 825 | 840 | 840 |
|---|---|---|---|---|---|
| | GHSV, (hr$^{-1}$) | 800 | 1,600 | 800 | 1,600 |
| Selectivity (%) | Ethane | 8.82% | 10.66% | 3.10% | 8.82% |
| | Ethylene | 28.29% | 30.73% | 16.01% | 28.29% |
| | Acetylene | 0.69% | 0.57% | 0.66% | 0.69% |
| | Propylene | 2.78% | 3.13% | 1.15% | 2.78% |
| | Propadiene | 0.06% | 0.05% | 0.03% | 0.06% |
| | Propane | 0.29% | 0.48% | 0.07% | 0.29% |
| | Methyl Acetylene | 0.29% | 0.25% | 0.19% | 0.29% |
| | C4's | 1.89% | 2.27% | 0.85% | 1.89% |
| | C5's | 0.00% | 0.04% | 0.00% | 0.00% |
| | C6$^+$'s | 1.55% | 1.59% | 1.70% | 1.55% |
| | Coke | ND | ND | ND | ND |
| Conversion (%) | Methane | 39.76% | 36.98% | 66.02% | 39.76% |
| Selectivity (%) | C$_2^+$ | 44.67% | 49.77% | 23.76% | 44.67% |
| Yield (%) | C$_2^+$ | 17.76% | 18.41% | 15.69% | 17.76% |
| Selectivity (%) | Carbon Dioxide | 51.83% | 46.94% | 73.74% | 51.83% |
| | Carbon Monoxide | 3.50% | 3.29% | 2.50% | 3.50% |
| Yield (%) | Carbon Dioxide | 20.61% | 17.36% | 48.68% | 20.61% |
| | Carbon Monoxide | 1.39% | 1.22% | 1.65% | 1.39% |
| Selectivity (%) | H$_2$ Selectivity (%) | 2.41% | 2.70% | 1.00% | 2.41% |
| | H$_2$O Selectivity (%) | 97.59% | 97.30% | 99.00% | 97.59% |

Example 5

An oxygen transfer agent as prepared in accordance with Example 2. The conversion of methane with this oxygen transfer agent, which contained CaSO$_4$, is shown below in Table 5. The observed yield of C2$^+$ product was 14-34%. This Example shows some of the benefits of using an oxygen transfer agent that contains CaSO$_4$ in accordance with aspects of the invention for the oxidative coupling of methane (OCM). For example, the methods of Example 5 (which used an oxygen transfer agent containing CaSO$_4$) provided improved olefin yields of at least 59.7% at a GHSV of 1,200 hr$^{-1}$ as compared to the methods of Example 4 (which used oxygen transfer agent containing a metal oxide without CaSO$_4$). Surprisingly, the methods of Example 5 provided a reduced olefin yield as compared to the method of Example 4 at a GHSV of 2,400 hr$^{-1}$.

TABLE 5

| TABLE V | Temp., (° C.) | 825 | 825 | 840 | 840 |
|---|---|---|---|---|---|
| | GHSV, (hr$^{-1}$) | 1,200 | 2,400 | 1,200 | 2,400 |
| Selectivity (%) | Ethane | 9.74% | 27.77% | 7.13% | 23.88% |
| | Ethylene | 53.71% | 50.66% | 49.57% | 52.38% |
| | Acetylene | 2.10% | 0.86% | 2.64% | 1.18% |
| | Propylene | 6.01% | 6.65% | 5.09% | 7.14% |
| | Propadiene | 0.21% | 0.17% | 0.23% | 0.23% |
| | Propane | 0.61% | 1.27% | 0.43% | 0.93% |
| | Methyl Acetylene | 0.58% | 0.40% | 0.62% | 0.54% |
| | C4's | 6.45% | 4.75% | 6.33% | 5.23% |
| | C5's | 1.96% | 1.96% | 2.15% | 1.84% |
| | C6$^+$'s | 1.63% | 0.70% | 3.94% | 0.87% |
| | Coke | ND | ND | ND | ND |
| Conversion (%) | Methane | 34.18% | 14.84% | 43.41% | 16.61% |
| Selectivity (%) | C$_2^+$ | 82.99% | 95.18% | 78.13% | 94.23% |
| Improved selectivity as compared to Table 4 (%) | C$_2^+$ | 85.8% | 91.2% | 228.8% | 110.9% |
| Yield (%) | C$_2^+$ | 28.37% | 14.12% | 33.92% | 15.65% |
| Improved yield as compared to Table 4 (%) | C$_2^+$ | 59.7% | −23.3% | 116.1% | −11.9% |
| Selectivity (%) | Carbon Dioxide | 11.92% | 3.61% | 14.95% | 3.98% |
| | Carbon Monoxide | 5.09% | 1.21% | 6.93% | 1.80% |
| Yield (%) | Carbon Dioxide | 4.07% | 0.54% | 6.49% | 0.66% |
| | Carbon Monoxide | 1.74% | 0.18% | 3.01% | 0.30% |

TABLE 5-continued

| | | | | | |
|---|---|---|---|---|---|
| Reduction as compared to Table 4 (%) | Carbon Dioxide | 80.3% | 96.9% | 86.7% | 96.8% |
| Reduction as compared to Table 4 (%) | Carbon Monoxide | −25.2% | 85.2% | −82.4% | 78.4% |
| Selectivity (%) | $H_2$ Selectivity (%) | 6.84% | 16.27% | 5.78% | 9.76% |
| | $H_2O$ Selectivity (%) | 93.16% | 83.73% | 94.22% | 90.24% |

Although the invention is illustrated and described herein with reference to specific embodiments, the invention is not intended to be limited to the details shown. Rather, various modifications may be made in the details within the scope and range of equivalents of the claims and without departing from the invention. Numerous variations, changes and substitutions will occur to those skilled in the art without departing from the spirit of the invention. Accordingly, it is intended that the appended claims cover all such variations as fall within the spirit and scope of the invention.

What is claimed is:

1. A method for producing one or more olefins from a hydrocarbon feed comprised of one or more alkanes, the method comprising:
a step of contacting a hydrocarbon feed comprised of one or more alkanes with an oxygen transfer agent at a temperature of 825° C. to 1000° C., wherein the oxygen transfer agent comprises i) an oxygen-donating chalcogen agent comprising at least one of a sulfate salt of an alkaline earth metal or a sulfate salt of an alkali metal, and a sulfate salt of manganese, and wherein the oxygen-donating chalcogen agent has an oxidation state greater than +2, and ii) a reducible metal oxide, wherein the oxygen-donating chalcogen agent and the reducible metal oxide are in solid form, and wherein water is formed from oxygen donated by the oxygen-donating chalcogen agent.

2. The method of claim 1, wherein the hydrocarbon feed comprises at least one of methane or ethane, and the produced one or more olefins comprises ethylene.

3. The method of claim 1, wherein the oxygen transfer agent comprises $Mg_6MnO_8$ and at least one promoter selected from the group consisting of Sm, Ga, Ti, W, Mo, V, Nb, Cr, K, Cs, Rb, P, Cu, Pb, Ni and As.

4. The method of claim 3, wherein the oxygen transfer agent further comprises boron or at least one compound thereof.

5. The method of claim 1, wherein the oxygen transfer agent additionally comprises at least one alkali metal or a compound thereof.

6. The method of claim 1, wherein the oxygen transfer agent additionally comprises at least one of an alkali metal oxide or an alkaline earth metal oxide.

7. The method of claim 1, wherein the oxygen transfer agent comprises a manganese oxide and wherein the manganese has a valence state of 4+, 3+, 8/3+, or 2+.

8. The method of claim 1, wherein the oxygen transfer agent comprises a) at least one compound selected from the group consisting of $NaB_2Mg_4Mn_2O_4$, $NaB_2Mn_2Mg_4O_{11.5}$, $NaMn_2O_4$, $LiMn_2O_4$, $Mg_3Mn_3B_2O_{10}$, $Mg_3(BO_3)_2$, and b) a non-crystalline compound comprising oxygen and at least one of sodium, boron, magnesium, manganese, or lithium.

9. The method of claim 1, wherein the reducible metal oxide is ionically and electronically conductive.

10. The method of claim 1, wherein at least 49% by moles of the hydrocarbon feed is converted to oxides of carbon, whereby water is produced as a co-product.

11. The method of claim 1, wherein at least 49% by moles of the hydrocarbon feed is converted to olefins, whereby water is produced as a co-product.

12. The method of claim 1, wherein the oxygen-donating chalcogen agent comprises calcium sulfate.

13. The method of claim 1, wherein a chalcogen of the oxygen-donating chalcogen agent has an oxidation state of +3 to +6.

14. The method of claim 13, wherein the chalcogen of the oxygen-donating chalcogen agent has an oxidation state greater than +3 and less than +6.

15. The method of claim 14, wherein the chalcogen of the oxygen-donating chalcogen agent has an oxidation state of +4.

16. The method of claim 1, wherein the oxygen transfer agent further comprises a sulfate salt of Sm, Ga, Ti, W, Mo, V, Nb, Cr, K, Cs, Rb, P, Cu, Pb, Ni, or As.

17. The method of claim 1, wherein the oxygen transfer agent is in a bed in a reactor and the gas hourly space velocity of the hydrocarbon feed to the bed is at least 600 $hr^{-1}$.

18. The method of claim 1, wherein a yield of ethylene is more than 67% by moles.

19. The method of claim 1, wherein the contacting takes place in an atmosphere substantially free of molecular oxygen.

20. The method of claim 1, wherein the contacting takes place in the presence of molecular oxygen.

21. The method of claim 1, wherein during the contacting step the oxygen transfer agent is converted to a reduced oxygen transfer agent and wherein the method comprises a further step of oxidizing the reduced oxygen transfer agent to regenerate the oxygen transfer agent.

22. The method of claim 1, wherein the hydrocarbon feed is contacted with the oxygen transfer agent at a temperature of 825° C. to 900° C.

23. The method of claim 1, further comprising introducing a feed comprising a gaseous compound of sulfur, the gaseous compound of sulfur having an oxidation state of 0 to −2, which acts to stabilize the oxygen transfer agent.

* * * * *